United States Patent [19]

Bernstein

[11] 4,055,167

[45] Oct. 25, 1977

[54] CURETTEMENT DEVICE

[76] Inventor: Dell L. Bernstein, 1295 Colorado Blvd., Denver, Colo. 80206

[21] Appl. No.: 679,675

[22] Filed: Apr. 23, 1976

[51] Int. Cl.² .................. A61B 1/00; A61B 17/22; A61M 1/00

[52] U.S. Cl. ..................... 128/2 B; 128/278; 128/304

[58] Field of Search .............. 128/2 B, 276, 304

[56] References Cited

U.S. PATENT DOCUMENTS

| 3,308,825 | 3/1967 | Cruse | 128/276 |
| 3,774,613 | 11/1973 | Woods, Jr. et al. | 128/304 |
| 3,889,657 | 6/1975 | Baumgarten | 128/276 X |
| 3,955,579 | 5/1976 | Bridgman | 128/304 |

Primary Examiner—Channing L. Pace

[57] ABSTRACT

A cannula for uterine curettement comprising a straight, rigid tube proportioned for insertion into the uterus, a flattened, closed end at the insert end of the tube and staggered openings at opposing sides of the tube adjacent to the insert end. A handle is provided at the opposite end to facilitate manipulation of the tube when it is in use and a short reach of the tube extends beyond this handle for attachment to the suction tube of an aspirator.

6 Claims, 5 Drawing Figures

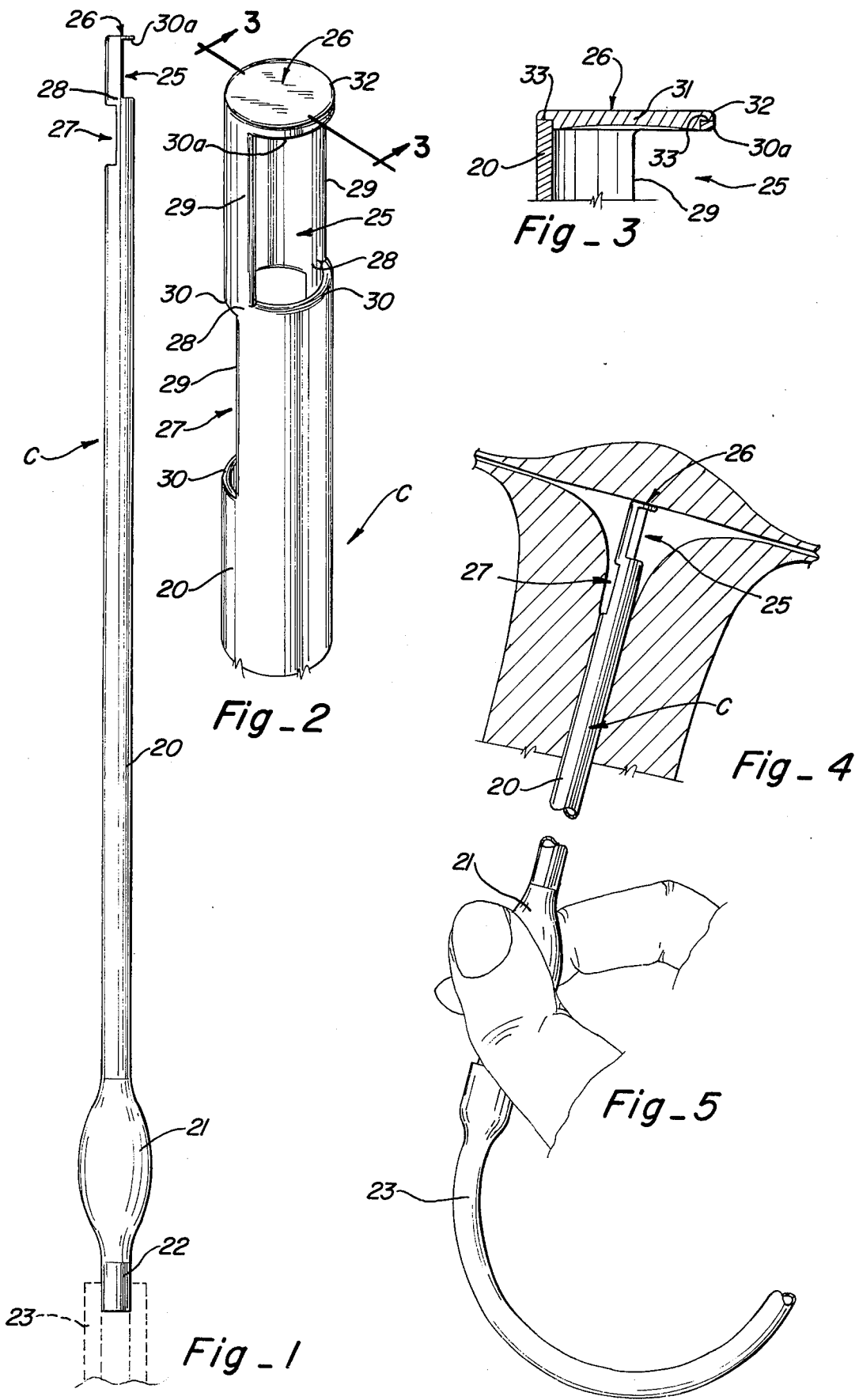

CURETTEMENT DEVICE

The present invention relates to apparatus for uterine curettement, and more particularly to cannulae for such purpose, the primary object of the invention being to provide a novel and improved construction of a cannula for uterine curettement.

PRIOR ART

The conventional types of cannulae for curettement are formed as moderately flexible, curved, plastic tubes to conform somewhat with the alignment of the uterine passageway for easy insertion therein, U.S. Pat. No. 3,769,980, patented Nov. 6, 1973, for Medical Instruments. The cannula is provided with opposing V-shaped openings near the operative end of the tube which are sized to permit applied suction to remove blood, serum and tissue as the curettement progresses. These cannulae are, also, provided with a pointed or rounded tip which extends some 1/4 inch or more beyond the adjacent opening. Comparison of equivalent plastic and metal cannulae is shown in International Journal of Gynaecology and Obstetrics, Vol. 13, 1975 No. 1, The Almqvist & Wiksell Periodical Company, Stockholm, Sweden.

A number of problems have arisen in the use of these cannulae. In the first place, the flexibility of the plastic, considered by some an advantage, prevents a physician form applying lateral pressure to the uterine walls at the end openings of the cannula. Also, this flexibility produces weakened portions of the wall between the staggered openings, causing the tubular structure to collapse, and as a result, the bent-over end of the cannula renders it comparatively ineffective. Furthermore, it has been found that the pointed tip of both types of cannulae prevents effective cleaning of the bottom, or the fundus of the uterus, at the points adjacent to the Fallopian tubes. It follows that while such cannulae are used extensively, there is, nevertheless, a need for an instrument of this type which avoids the above mentioned disadvantages, and which is a better performer, especially in difficult cases where considerable probing and prodding is required to effectively complete the curettement.

THE INVENTION

The present invention was conceived and developed to meet such a need, that is, to provide an improved cannula for uterine curettement. As such, the invention comprises, in essence, a rigid, straight, tube having opposing, staggered side openings at its operative end with a flattened end and with the first side opening being immediately adjacent to this end. It was discovered that in use, the straight cannula presented no problem of insertion for the uterus which easily flexes to accommodate the same. The advantages gained by lateral manipulation of the rigid tube far offset any supposed advantage of a moderately flexible tube. For example, the rigid tube permits lateral pressure to be applied against the uterus wall and the fundus in ways not at all possible with a flexible tube.

OBJECTS OF THE INVENTION

Accordingly, it follows that the objects of the invention are to provide a novel and improved cannula for uterine curettement which can be used without concern as to the possibility of the cannula collapsing in the portion between the opposing openings, which can apply lateral pressure at its end for more effective curettement movements, which easily reaches the fundus of the uterus and the wall portions alongside the Fallopian tubes, and which is a simple, neat appearing, effective economical instrument. Other objects includes the reusability of the unit, when made of stainless steel, easy cleaning and sterilization, etc.

GENERAL DESCRIPTION OF THE DRAWINGS

With the foregoing and other objects in view, my present invention comprises certain constructions, combinations and arrangements of parts and elements as hereinafter described, defined in the appended claims, and illustrated in preferred embodiment by the accompanying drawing in which:

FIG. 1 is a longitudinal view of an improved cannula constructed according to the principles of the invention.

FIG. 2 is an isometric view of the operative end of the cannula shown at FIG. 1, but on an enlarged scale.

FIG. 3 is a fragmentary sectional detail as taken from the indicated line 3—3 at FIG. 2, but on a further enlarged scale.

FIGS. 4 and 5 are a diagrammatic view, with portions broken away to conserve space and showing the cannula as being inserted into the uterus cavity hand held in position and with an aspirator tube connected thereto as when the instrument is being used.

SPECIFIC DESCRIPTION OF THE INVENTION

Referring more particularly to the drawings, the improved cannula C is formed as a rigid tube 20 of metal, preferably of stainless steel or of a type which will not affect bodily tissue in any manner and which will not corrode or discolor. A very suitable metal is various types of stainless steel. The tube 20 is proportioned to fit into the uterine passageway from the cervix and to the bottom of the uterine cavity, as in the manner shown at FIG. 4. As such, the tube is approximately 1/4 inch (6 millimeters) in diameter, and the wall thickness, approximately 0.050 inch (1 millimeter), is such as to provide adequate strength and rigidity for handling and manipulating the instrument. The length of this tube 20 is 10 to 12 inches long, sufficient to be fully inserted into the uterus with an additional portion to permit a physician to hold and manipulate the instrument. A handle 21 is provided at this outer end of the instrument with a short portion 22 beyond the end of the handle 21 to provide connection to an aspirator tube 23.

The suction openings at the operative end of the tube 20 are formed as a pair of rectangular cutouts which oppose each other, the first opening 25 being adjacent to a flat end 26 of the instrument and the second opening 27 being positioned beyond the first in a staggered pattern with a structural neck 28 at each side of and between the openings sufficient to provide adequate structural strength and rigidity. Each opening cuts out approximately an 150° arc from the wall of the tube to render its transverse width slightly less than the diameter of the tube, approximately 1/4 inch, while the height of each opening is approximately 1/2 inch, twice the tube diameter. The aforementioned neck 28 may be anywhere from 1/16 to 1/8 inch.

The outer edges of each opening, the longitudinal sides 29 and the circular ends 40, are squared, moderately sharp, smooth corners which can effectively scrape away unwanted tissue without damaging the remaining tissue. The end 26 of this instrument is closed by a disc-shaped cap 31 having a thickness approximately 1/20 inch, more or less, with the outer corner 32 of this circular cap being rounded somewhat but with the inner edge 30a at the first mentioned opening 25 being a smooth but comparatively sharp corner, the same as heretofore described. This end cap 31 may be fastened onto the tube in any suitable manner, as by a steplike joint 33 with a radial flange portion of the cap seated of the tube 20 covering the opening. The cap 31 may be soldered or welded in place at this opening or secured in any other suitable manner, illustrated at FIG. 3.

The handle 21 at the opposite end of the cannula tube may be formed in any suitable manner to assist in gripping and manipulating the same. Preferably, this handle 21 is an ovoid, bulbous knob formed concentrically upon the tube and having a diameter from ½ to ¾ inch at its equator. This rounded construction permits the physician to easily hold, manipulate or turn the cannula whenever desired.

In use, when the cannula C is inserted into the uterine cavity, as diagrammatically indicated at FIG. 4, the physician holding the tube, as in the manner illustrated, may easily insert and move the tube back and forth longitudinally with the flat bottom 26 abutting against the fundus portion of the uterus and with the circular end edges 30 of the openings 25 and 27 providing an effective scraping movement against the walls of the uterine cavity. In addition to this reciprocal movement, the cannula may be rotated to expose the openings to any portion of the uterus wall and, also, provide scraping actions by the opening edges 29. Because of the rigidity of the unit, the cannula may be pressed laterally or tipped against the sides of the uterus in any direction to provide some lateral pressure against the walls of the uterus as the curettement operation progresses. Also, the flat end 26 may be pushed against the bottom or the fundus of the uterus, moved laterally and rotated to various positions to curette this portion of the fundua. Suction will be applied to this cannula in a continuous manner throughout the entire curettement operation in a conventional manner to continuously remove blood, serum and tissue.

A cannula configuration, in accordance with the present invention, was used extensively for a large number of abortions. A six mm outside diameter cannula was found highly effective for terminating abortions up to about 2½ months from missed periods. The small size is highly important as dialation need only be slightly larger than the cannula, which may be accomplished at the same time of the curettement. The edges of the opposed openings give better scraping and the end provides scraping of the fundus which can not be accomplished with the prior cannulae with the pointed elongated ends. The rotation of the cannula provides highly effective scraping. Also, with the smaller cannulae, syringe suction is effective for removal of the products of the curettage.

I have now described my invention in considerable detail. However, it is obvious that others skilled in the art can build and devise alternate and equivalent constructions which are nevertheless within the spirit and scope of my invention. Hence, I desire that my protection be limited, not by the constructions illustrated and described, but only by the proper scope of the appended claims.

What is claimed is:

1. A cannula for uterine curettement comprising:
   a. a straight, rigid tube proportioned for insertion into the uterus with an excess of length to provide a handle section and a connective section therebeyond for the connection of a suction tube;
   b. an enlargement at the handle section to facilitate gripping of the tube;
   c. a flattened, thin walled, closed end permanently affixed at the insert end of the tube; and
   d. a first opening, having a width slightly less than the tube diameter, immediately adjacent to the flattened end of the tube and a second opening of approximately the dimensions of the first opening, axially spaced along the tube from the first opening and on the opposite side of the tube from the first opening with the edges of the openings squared, moderately sharp and generally smooth to facilitate curettement action, and with the openings proportioned to receive blood, serum and tissue from the uterus.

2. The cannula defined in claim 1 wherein the tube has a circular cross section and the width of each opening is through an approximate 150 degree arc to approach the diameter of the tube.

3. The cannula defined in claim 2, wherein each opening has two parallel side edges along the cannula axis, and two parallel end edges perpendicular to the cannula axis, with the length of the side edges approximately twice the length of the end edges.

4. The cannula defined in claim 3, wherein the insert end is formed as a thin disc closing the tube and forming the adjacent edge of said first opening, with the edge of the disc end being rounded defining a circular edge of the opening and being axially squared, moderately sharp and smooth to facilitate curettement action. action.

5. The cannula defined in claim 3, including said second opening at the opposite side of the tube is axially staggered with respect to the first and spaced from and closely adjacent to the first, and with a neck portion in the wall of the tube at each side of and between the openings proportioned to provide adequate structural strength and rigidity to the unit.

6. The cannula defined in claim 1, wherein the handle is an ovoid form to facilitate manipulation and rotating the same when in use.

* * * * *